United States Patent
Wang

(10) Patent No.: US 8,569,492 B2
(45) Date of Patent: Oct. 29, 2013

(54) METHOD FOR PREPARING HALOFUGINONE DERIVATIVE

(76) Inventor: Xiaoqi Wang, Zhejiang (CN)

( * ) Notice: Subject to any disclaimer, the term of this patent is extended or adjusted under 35 U.S.C. 154(b) by 0 days.

(21) Appl. No.: 13/496,936

(22) PCT Filed: Sep. 12, 2010

(86) PCT No.: PCT/CN2010/076821
§ 371 (c)(1),
(2), (4) Date: Mar. 19, 2012

(87) PCT Pub. No.: WO2011/032474
PCT Pub. Date: Mar. 24, 2011

(65) Prior Publication Data
US 2012/0178929 A1    Jul. 12, 2012

(30) Foreign Application Priority Data
Sep. 21, 2009   (CN) .......................... 2009 1 0152696

(51) Int. Cl.
*C07D 239/72*    (2006.01)
*C07D 401/00*    (2006.01)

(52) U.S. Cl.
USPC .......................................... 544/284; 544/283

(58) Field of Classification Search
USPC .................................................. 544/283, 284
See application file for complete search history.

(56) References Cited

U.S. PATENT DOCUMENTS 6,420,372 B1    7/2002 Kobayashi et al.

FOREIGN PATENT DOCUMENTS

| CN | 1179358 A | 4/1998 |
|----|-----------|--------|
| CN | 101648942 A | 2/2010 |
| ZA | 200410045471 | 7/2006 |

*Primary Examiner* — Paul V. Ward
(74) *Attorney, Agent, or Firm* — Jacobson Holman PLLC; Jiwen Chen

(57) ABSTRACT

A method for preparing a halofuginone derivative, in particular a method for preparing an inhibitor medicament expressed by specific I-type procollagen in the invention a condensate of formula (II) reacts for 12-35 hours in a catalytic hydrogenation solvent with the existence of Ni—B amorphous alloy catalyst, at the hydrogen pressure of 0.1-10 Mpa and at the temperature of 10-60° C., and then the catalyst is filtered, the filtrate is decompressed to recover the solvent, the pH value is regulated to obtain a crude product of formula (I), and the crude product of the formula (I) is refined to obtain a refined product of formula (I).

13 Claims, No Drawings

METHOD FOR PREPARING HALOFUGINONE DERIVATIVE

TECHNICAL FIELD

The present invention involves with a chemical preparation method, specifically a preparation method of an inhibitor of specific collagen type I gene expression.

TECHNICAL BACKGROUND

According to WHO reports, malaria is the most serious known infectious disease, with incidence of 300-600 million cases per year globally and mortablity of 3 million, particularly common among African infants and other vulnerable populations. Although existing drugs such as quinoline, chloroquine, etc have some effects on malaria, the human body will rapidly generate resistance during treatments. Nevertheless, ancient Chinese people used the Saxifragaceae herb Dichroa febrifuga (Chang Shan) to cure malaria. In 1950s, Chinese scientists extracted febrifugine from the plant and discovered its anti-malarial activity. The absolute configuration of its compound, however, was not finally determined until 1999 through chiral synthesis.

Halofuginone derivative, as an inhibitor of specific type I collagen gene expression, may play a role in many fiber cells and inhibit collagen expression synthesis in experimental fibrosis models of liver, lung, derma and uterus. The most important halofuginone derivatives are Halofuginone and Febrifugine. As Halofuginone plays a role in specific collagen transcription, it is a promising anti-hepatic fibrosis agent. In 2002, Tempostatin® (Halofuginone hydrobromide) developed by Collgard Biopharms was approved in Europe as a new orphan drug for treatment of systemic sclerosis. RU-19110 developed by a French company, Roussel Ucla, has entered clinical study.

Currently, synthesis of halofuginone derivatives generally refers to procedures developed by Japanese scientist Takeuchi Y (Chemical Communication, 2000, 1643-1644), which applies enzyme reduction to get key chiral intermediate, then obtain bromide A via a four-step reaction, and finally obtain CBZ-protected halofuginone derivative (3-)[[(3aR,7aS)-N-CBZ-2-hydroxyl-Octahydro furan and [3,2-b]2-Piperidinyl] methyl]-4(3H)-quinazolinone) through condensation (as shown in structural formula II). In his method, deprotection is performed as palladium hydroxide-catalyzed hydrogenation. The method includes 11 steps, with a total yield of 5.88%. However, side reactions will occur when using palladium hydroxide-catalyzed hydrogenation as deprotection, e.g., carbon-nitrogen double bond in the quinazolinone structure will be reduced additively to produce by-products such as C1; if quinazolinone structure contains bromine and chlorine, it is easier to be deprotected to produce by-products such as C2 and C3. Therefore, this method is not applicable to commercial production of Halofuginone.

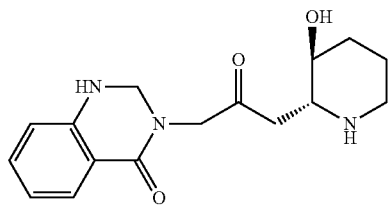

C1

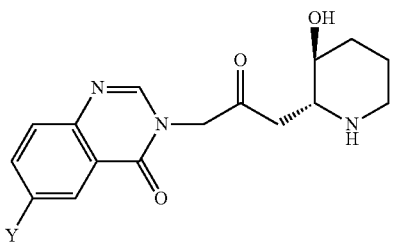

C2

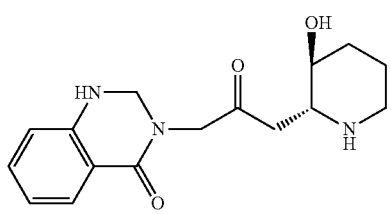

C3

Haruhisa K et al. also reported that palladium on carbon catalytic hydrogenation process is not applicable to some halofuginone derivatives, and acid reflux method for deprotection is not applicable to condensate (II) as hydroxyl in the condensate structure is easy to be removed (*J. Med. Chem.*, 2006, 49, 4698). Only hydroxyl in the condensate structure firstly protected can then strong acid reflux method to be used in deprotection (U.S. Pat. No. 6,420,372).

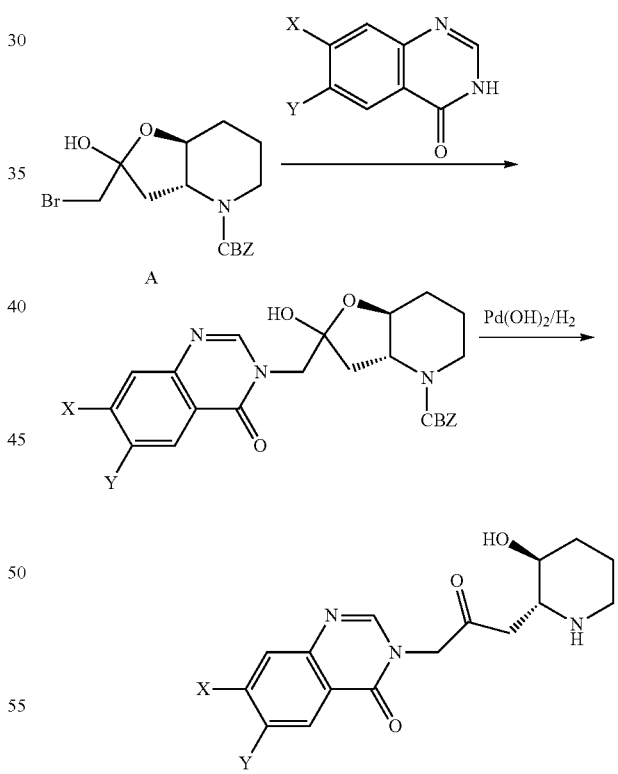

Febrifugine X = H, Y = H;
Halofuginone X = Br, Y = Cl;

Kobayashi S. reported a method which uses chiral formaldehyde as raw material to obtain hydroxyl-protected piperidine bromide B via synthesis, followed by condensation to obtain hydroxyl-protected condensate V, then use palladium on carbon catalytic hydrogenation and acid, respectively, to deprotect CBZ and $R_1$ (U.S. Pat. No. 6,420,372 and *J. Org.*

Chem., 1999, 64, 6833). The process uses expensive catalyst to synthesize hydroxyl-protected piperidine bromide B but with low yield, so the process is only applicable to lab-scale preparation of halofuginone derivative rather than commercial production.

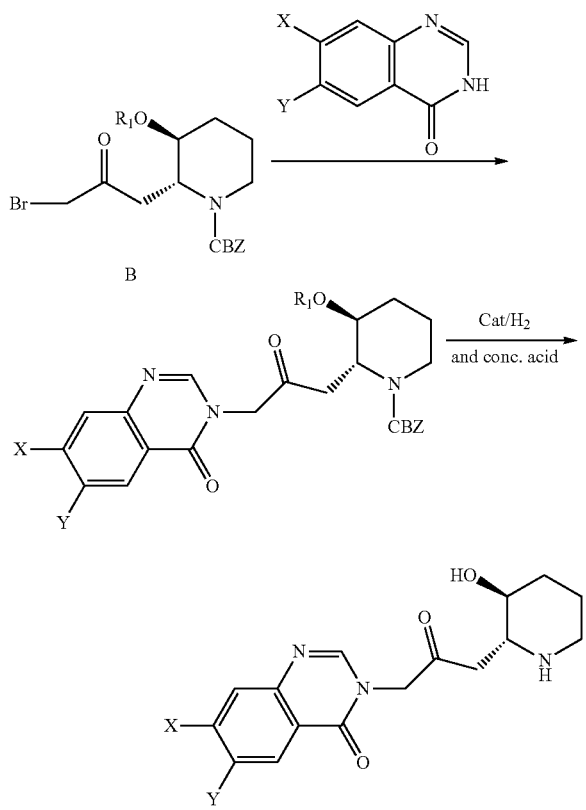

R₁ = Me, Et, CH₂Ph,
Febrifugine X = H, Y = H;
Halofuginone X = Br, Y = Cl;

Chinese Patent No. ZL200410045471 and Taniguchi T. et al. (*Org. Lett.*, 2000, 2, 3193) reported that take epoxy compound C of piperidine structure as a key intermediate, condense it with quinolinone, obtain condensate V via Dess-Martin oxidation, and then obtain halofuginone derivative after deprotection by hydrogenation or acid. This method not only needs 10 steps to obtain epoxy compound 3, but also needs rare metal with a total yield of 11%. Furthermore, the application of RCM reaction and rare metal limits its commercial use.

$R_1$ = Me, Et, CH₂Ph,
Febrifugine X = H, Y = H;
Halofuginone X = Br, Y = Cl;

Therefore, developing an effective and simple method to deprotect CBZ in condensate (II) is key to synthesize halofuginone via chemical methods. The present invention for the first time proposes Ni—B non-crystalline alloy as catalyst to deprotect CBZ via catalytic hydrogenation.

INVENTION CONTENT

The present invention develops a production method with higher efficiency and simpler process to overcome current technical deficiencies.

The present invention adopts the following technical solution, i.e. a preparation method of 3-[3-[(2R,3S)-3-hydroxyl-2-piperidinyl]-2-oxypropyl]-4(3H)-quinazolinone derivative as shown in formula (I). This solution includes steps as follows: Condensate shown in formula (II) fully reacts in the catalytic hydrogenation solvent under 0.1~1.0 MPa controlled hydrogen pressure and 10~60° C., with presence of Ni—B non-crystalline alloy catalyst; then filter the catalyst, reduce pressure on the yielded filtrate to recover the solvent, and add 300 ml water to adjust pH value within 9~10; then obtain 3-[3-[(2R,3S)-3-hydroxyl-2-piperidinyl]-2-oxypropyl]-4(3H)-quinazolinone derivative (I) crude which can be further refined to be refined form. The said Ni—B non-crystalline alloy catalyst is prepared by loading Ni—B non-crystalline alloy on aluminium oxide or zeolite carrier, with a load of 1.0~20.0%, the mass ratio between the said Ni—B non-crystalling alloy catalyst and condensate (II) is 1:10~40; the said catalytic hydrogenation solvent is 0.1~0.4N acidic aqueous alcohol solution.

Detailed steps, as well as features, are as follows:
(1) The condensate shown in formula (II) is a raw material, which fully reacts for 12-35 hours in the catalytic hydrogenation solvent with the presence of Ni—B non-crystalline alloy catalyst, under conditions of 0.1~1.0 MPa controlled hydrogen pressure and temperature of 10~60° C. This catalytic hydrogenation time, 12-35 hours, may depend on raw material reaction status which need to be traced by liquid chromatography.

A complete reaction is shown as the following formula:

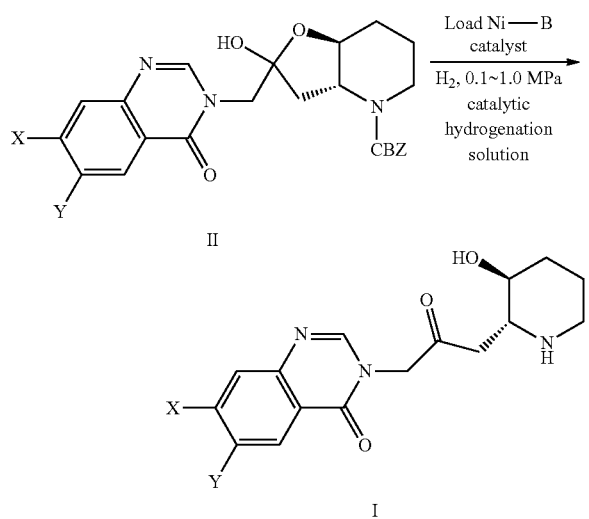

Halofuginone and its derivative
X = H, Y = H;
X = Br, Y = Cl;

Through the above-mentioned hydrogenation process, double bond reduction product C3 and dehalogenated products C1 and C2 can be obtained with low contents along with crude product. The yielded crude can be further refined to get high purity product 3-[3-[(2R,3S)-3-hydroxyl-2-piperidinyl]-2-oxypropyl]-4(3H)-quinazolinone derivative.

The said Ni—B noncrystalline alloy catalyst is prepared by loading Ni—B non-crystalline alloy on aluminium oxide or zeolite carrier, with a load of 1.0~20.0% (as weight percentage);

The mass ratio between the Ni—B non-crystalline alloy catalyst and condensate (II) is 1:10~40;

The catalytic hydrogenation solvent is 0.1~0.4N acidic aqueous alcohol solution and the mass required of which is 8-20 times that of the condensate (II);

The Ni—B non-crystalline alloy catalyst is prepared as follows: add nickel salt into the aqueous solvent until it is dissolved; then add carrier, such as aluminium oxide or zeolite; $KBH_4$ solution should be added drip by drip under 0~30° C.; after reaction over, filter the solution, wash the precipitates with deionized water until pH value reaches 6.5~7.5, and finally store the treated precipitates in anhydrous ethanol for use; the nickel salt above is optional among $Ni(NO_3)_2$, $NiCl_2$ or $Ni(SO_4)_2$;

(2) Filter the catalyst and treat the yielded filtrate appropriately before obtaining 3-[3-[(2R,3S)-3-hydroxyl-2-piperidinyl]-2-oxypropyl]-4(3H)-quinazolinone derivative (I) crude;

(3) Through refining procedures, obtain the refined 3-[3-[(2R, 3S)-3-hydroxyl-2-piperidinyl]-2-oxypropyl]-4(3H)-quinazolinone derivative (I) from crude;

The refining procedures are as follows: add the 3-[3-[(2R, 3S)-3-hydroxyl-2-piperidinyl]-2-oxypropyl]-4(3H)-quinazolinone derivative crude to the re-crystallizing solvent for reflux for more than 8 hours, then decolorise it with activated carbon and crystallize it under 0~40° C. for 3-8 hours; finally the refined product can be obtained;

The selected re-crystallizing solvent is a mixed solution of alcohol, water and halohydrocarbon. The mixed solvent requires 5-15 times of the 3-[3-[(2R,3S)-3-hydroxyl-2-piperidinyl]-2-oxypropyl]-4(3H)-quinazolinone derivative crude in weight;

The ratio of the mixed solvent for the re-crystallization is: the mass ratio of alcohol:water:halohydrocarbon=1:0.1~0.3: 0.05~0.2:Alcohol used in the solvent for the re-crystallization is C1~C4 alcohol;

Halohydrocarbon used in the solvent for the re-crystallization is optional among dichromethane, trichloromethane, dichroethane or carbon tetrachloride.

Preferably in the preparation method of the present invention, the said catalyst is Ni—B non-crystalline alloy catalyst prepared by loading Ni—B non-crystalline alloy on aluminium oxide or zeolite carrier, with a load of 1.0~10.0%.

Preferably in the preparation method of the present invention, the mass ratio between the said Ni—B non-crystalline alloy catalyst and condensate (II) is 1:10~20.

Preferably in the preparation method of the present invention, the number of re-using the said Ni—B non-crystalline alloy on aluminium oxide or zeolite carrier is 5-10 times.

Preferably in the preparation method of the present invention, the mass required for the catalytic hydrogenation solvent is 8-15 times that of the condensate (II).

Preferably in the preparation method of the present invention, the acid used in the said catalytic hydrogenation solvent is optional among $H_2SO_4$, hydrochloric acid, formic acid or acetate.

Preferably in the preparation method of the present invention, the said catalytic hydrogenation solvent is 0.4N acidic aqueous alcohol solvent, and the alcohol is optional among methanol, ethanol, isopropyl alcohol, n-butanol, isobutanol, tert-butanol or amyl alcohol;

The mass of water contained in the said aqueous alcohol solvent is 5~30% that of the alcohol.

Preferably in the preparation method of the present invention, the hydrogen pressure during catalytic hydrogenation is 0.1~0.6 Mpa and the catalytic hydrogenation temperature is 10~60° C.

Preferably in the preparation method of the present invention, the said catalytic hydrogenation time is 15-25 hours.

Preferably in the preparation method of the present invention, the ratio among nickel salt, carrier and KBH4 during step (1), the preparation process of the Ni—B non-crystalline alloy catalyst, is 0.02~1.0:0.8~1.2:1.0 (in mol), and the temperature for reduction reaction is 0~10° C.

Preferably in the preparation method of the present invention, the selected re-crystallizing solvent as described in step (3) is a mixed solution of alcohol, water and halohydrocarbon, and this mixture requires 5-10 times of 3-[3-[(2R,3S)-3-hydroxyl-2-piperidinyl]-2-oxypropyl]-4(3H)-quinazolinone derivative crude in weight.

Preferably in the preparation method of the present invention, the alcohol used in the re-crystallizing solvent as described in step (3) is optional among methanol, ethanol isopropyl alcohol or propyl alcohol.

Preferably in the preparation method of the present invention, the crystallization temperature as described in step (3) is 0~15° C.; the crystallization time is 3-5 hours.

Compared with existing technologies, the present invention has benefits as follows:
(1) The Ni—B non-crystalline alloy catalyst carried on aluminium oxide or zeolite applied in the present invention can be reused without losing activity. Catalytic hydrogenation under common or reduced pressure can inhibit the generation of by-products and therefore substantially improves the reaction selectivity.

(2) The present invention provides a simple refining method which improves product quality and can be applied to large-scale commercial production.

SPECIFIC OPERATIONS

The following details the preparation of the Ni—B non-crystalline alloy catalyst with examples:

Example 1

Add 0.67 mol of Ni(NO$_3$)$_2$ into a four-neck flask, add 100 g aluminium oxide, then add 1.0 mol of KBH$_4$ solution drip by drip while stirring in 0° C. When the drip feed ends, keep it in reaction until no gas is released, then stop the reaction. Filter it, repeatedly wash the black precipitate with deionized water until pH=7, then wash it for four times with anhydrous ethanol and finally store it in anhydrous ethanol for use.

Example 2

Add 0.33 mol of Ni(NO$_3$)$_2$ to a four-neck flask, and add 100 g zeolite, add 1.0 mol of KBH$_4$ solution drip by drip while stirring in 10° C. When the drip feed ends, keep it in reaction until no gas is released, then stop the reaction. Filter it, repeatedly wash the black precipitate with deionized water until pH=7.2, then wash it for six times with anhydrous ethanol and finally store it in anhydrous ethanol for use.

Example 3

Add 0.033 mol of Ni(NO$_3$)$_2$ into a four-neck flask, add 100 g aluminium oxide, then add 1.0 mol of KBH$_4$ solution drip by drip while stirring in 10° C. When the drip feed ends, keep it in reaction until no gas is released, then stop the reaction. Filter it, repeatedly wash the black precipitate with deionized water until pH=7.4, then wash it for eight times with anhydrous ethanol and finally store it in anhydrous ethanol for use.

Example 4

Add 0.1 mol of Ni(NO$_3$)$_2$ into a four-neck flask, add 100 g zeolite, then add 1.0 mol of KBH$_4$ solution drip by drip while stirring in 30° C. When the drip feed ends, keep it in reaction until no gas is released, then stop the reaction. Filter it, repeatedly wash the black precipitate with deionized water until pH=6.5, then wash it for six times with anhydrous ethanol and finally store it in anhydrous ethanol for use.

Example 5

Add 0.5 mol of Ni(NO$_3$)$_2$ into a four-neck flask, add 100 g aluminium oxide, then add 1.0 mol of KBH$_4$, solution drip by drip while stirring in 10° C. When the drip feed ends, keep it in reaction until no gas is released, then stop the reaction. Filter it, repeatedly wash the black precipitate with deionized water until pH=6.8, then wash it for nine times with anhydrous ethanol and finally store it in anhydrous ethanol for use.

Example 6

Take 20 g condensate (II), i.e. (3-)[[(3aR,7aS)-N-CBZ-2-hydroxyl-Octahydro furan and [3,2-b]2-Piperidinyl]methyl]-4(3H)-quinazolinone), dissolve it with 160 g 0.4N sulfuric acid-methanol solution (water content is 5%), add 2 g Ni—B non-crystalline alloy catalyst carried on aluminium oxide at 1.0% (as prepared in Example 1), hydrogenate it under 10° C. and 0.1 Mpa hydrogen pressure, keep it in reaction for 35 hours, then filter it to recover Ni—B non-crystalline alloy catalyst, wash the catalyst with 50 ml methanol, reduce pressure to recover the solvent, add 300 ml water, adjust the pH value to 9~10, then stir and filter it in room temperature to obtain 3-[3-[(2R,3S)-3-hydroxyl-2-piperidinyl]-2-oxypropyl]-4(3H)-quinazolinone (I) crude. The yield rate is 65.2%, with content by HPLC of 93.2% and C1 of 4.2%.

Example 7

Take 20 g condensate (II), (3-)[[(3aR,7aS)-N-CBZ-2-hydroxyl-Octahydro furan and [3,2-b]2-Piperidinyl]methyl]-4(3H)-quinazolinone), dissolve it with 300 g 0.4N hydrochloric acid-methanol solution (water content is 10%), add 1 g Ni—B non-crystalline alloy catalyst carried on zeolite with a load of 5.0% (as prepared in Example 2), hydrogenate it under 60° C. and 0.3 Mpa hydrogen pressure, keep it in reaction for 12 hours, then filter it to recover Ni—B non-crystalline alloy catalyst, wash the catalyst with 50 ml ethanol, reduce pressure to recover the solvent, add 300 ml water, adjust the pH value to 9~10, then stir and filter it in room temperature to obtain 3-[3-[(2R,3S)-3-hydroxyl-2-piperidinyl]-2-oxypropyl]-4(3H)-quinazolinone (I) crude. The yield rate is 52.1%, with content by HPLC of 71.2% and C1 of 3.2%.

Example 8

Take 20 g condensate (II), 7-bromine-6-chlor-(3-)[[(3aR,7aS)-N-CBZ-2-hydroxyl-Octahydro furan and [3,2-b]2-Piperidinyl]methyl]-4(3H)-quinazolinone), dissolve it with 400 g 0.4N formic acid-isopropyl alcohol solution (water content is 15%), add 0.8 g Ni—B non-crystalline alloy catalyst carried on aluminium oxide with a load of 8.0% (as prepared in Example 3), hydrogenate it under 30° C. and 0.5 Mpa hydrogen pressure, keep it in reaction for 10 hours, then filter it to recover Ni—B non-crystalline alloy catalyst, wash the catalyst with 50 ml isopropyl alcohol, reduce pressure to recover the solvent, add 350 ml water, adjust the pH value to 9~10, then stir and filter it in room temperature to obtain 7-bromine-6-chlor-3-[3-[(2R,3S)-3-hydroxyl-2-piperidinyl]-2-oxypropyl]-4(3H)-quinazolinone (I) crude. The yield rate is 76.3%, with content by HPLC of 92.2% as well as C1: 0.8%, C2: 3.8% and C3: 1.2%.

Example 9

Take 20 g condensate (II), (3-)[[(3aR,7aS)-N-CBZ-2-hydroxyl-Octahydro furan and [3,2-b]2-Piperidinyl]methyl]-4(3H)-quinazolinone), dissolve it with 300 g 0.4N acetate/n-butanol solution (water content is 30%), add 0.5 g Ni—B non-crystalline alloy catalyst carried on aluminium oxide with a load of 10.0% (as prepared in Example 4), hydrogenate it under 50° C. and 1.0 Mpa hydrogen pressure, keep it in reaction for 25 hours, then filter it to recover Ni—B non-crystalline alloy catalyst, wash the catalyst with 50 ml n-butanol, reduce pressure to recover the solvent, add 300 ml water, adjust the pH value to 9~10, then stir and filter it in room temperature to obtain 3-[3-[(2R,3S)-3-hydroxyl-2-piperidinyl]-2-oxypropyl]-4(3H)-quinazolinone (I) crude. The yield rate is 85.2%, with content by HPLC of 94.2% and C1: 2.9%.

Example 10

Take 20 g condensate (II), (3-)[[(3aR,7aS)-N-CBZ-2-hydroxyl-Octahydro furan and [3,2-b]2-Piperidinyl]methyl]-4(3H)-quinazolinone), dissolve it with 200 g 0.1N acetate-isobutanol solution (water content is 25%), add 0.8 g Ni—B non-crystalline alloy catalyst carried on zeolite with a load of 20.0% (as prepared in Example 5), hydrogenate it under 40° C. and 0.8 Mpa hydrogen pressure, keep it in reaction for 15 hours, then filter it to recover Ni—B non-crystalline alloy catalyst, wash the catalyst with 50 ml isobutanol, reduce pressure to recover the solvent, add 300 ml water, adjust the pH value to 9~10, then stir and filter it in room temperature to obtain 3-[3-[(2R,3S)-3-hydroxyl-2-piperidinyl]-2-oxypropyl]-4(3H)-quinazolinone (I) crude. The yield rate is 82.5%, with content by HPLC of 94.2% and C1 of 1.2%.

Example 11

Take 20 g condensate (II), 7-bromine-6-chlor-(3-)[[(3aR,7aS)-N-CBZ-2-hydroxyl-Octahydro furan and [3,2-b]2-Piperidinyl]methyl]-4(3H)-quinazolinone), dissolve it with 250 g 0.3N $H_2SO_4$ acetate-tert-butyl alcohol solution (water content is 20%), add 1.2 g Ni—B non-crystalline alloy catalyst carried on aluminium oxide with a load of 15.0%, hydrogenate it under 40° C. and 0.6 Mpa hydrogen pressure, keep it in reaction for 20 hours, then filter it to recover Ni—B non-crystalline alloy catalyst, wash the catalyst with 50 ml tert-butyl alcohol, reduce pressure to recover the solvent, add 300 ml water, adjust the pH value to 9~10, then stir and filter it in room temperature to obtain 7-bromine-6-chlor-3-[3-[(2R,3S)-3-hydroxyl-2-piperidinyl]-2-oxypropyl]-4(311)-quinazolinone (I) crude. The yield rate is 78.5%, with content by HPLC of 93.6% as well as C1: 0.6%, C2: 3.1% and C3: 1.5%.

Example 12

Take 20 g condensate (II), 7-bromine-6-chlor-(3-)[[(3aR,7aS)-N-CBZ-2-hydroxyl-Octahydro furan and [3,2-b]2-Piperidinyl]methyl]-4(3H)-quinazolinone), dissolve it with 350 g 0.4N hydrochloric acid-amyl alcohol solution (water content is 10%), add 2 g Ni—B non-crystalline alloy catalyst carried on zeolite with a load of 5.0%, hydrogenate it under 50° C. and 1.0 Mpa hydrogen pressure, keep it in reaction for 20 hours, then filter it to recover Ni—B non-crystalline alloy catalyst, wash the catalyst with 50 ml amyl alcohol, reduce pressure to recover the solvent, add 300 ml water, adjust the pH value to 9~10, then stir and filter it in room temperature to obtain 7-bromine-6-chlor-3-[3-[(2R,3S)-3-hydroxyl-2-piperidinyl]-2-oxypropyl]-4(3H)-quinazolinone (I) crude. The yield rate is 80.5%, with content by HPLC of 94.6% as well as C1: 0.6%, C2: 2.5% and C3: 1.1%.

Example 13

Take 20 g condensate 7-bromine-6-chlor-(3-)[[(3aR,7aS)-N-CBZ-2-hydroxyl-Octahydro furan and [3,2-b]2-Piperidinyl]methyl]-4(3H)-quinazolinone), dissolve it with 250 g 0.4N acetate-methanol solution (water content is 10%), add 2 g Ni—B non-crystalline alloy catalyst carried on aluminium oxide with a load of 8.0%, hydrogenate it under 60° C. and 1.0 Mpa hydrogen pressure, keep it in reaction for 25 hours, then filter it to recover Ni—B non-crystalline alloy catalyst, wash the catalyst with 50 ml methanol, reduce pressure to recover the solvent, add 300 ml water, adjust the pH value to 9~10, then stir and filter it in room temperature to obtain 7-bromine-6-chlor-3-[3-[(2R,3S)-3-hydroxyl-2-piperidinyl]-2-oxypropyl]-4(3H)-quinazolin one (I) crude. The yield rate is 83.5%, with content by HPLC of 95% as well as C1: 0.4%, C2: 1.5% and C3: 1.0%.

Example 14

Take 20 g condensate 7-bromine-6-chlor-(3-)[[(3aR,7aS)-N-CBZ-2-hydroxyl-Octahydro furan and [3,2-b]2-piperidinyl]methyl]-4(3H)-quinazolinone), dissolve it with 250 g 0.4N acetate-ethanol solution (water content is 10%), add 1.5 g Ni—B non-crystalline alloy catalyst carried on aluminium with a load of 10.0%, hydrogenate it under 50° C. and 1.0 Mpa hydrogen pressure, keep it in reaction for 30 hours, then filter it to recover Ni—B non-crystalline alloy catalyst, wash the catalyst with 50 ml ethanol, reduce pressure to recover the solvent, add 300 ml water, adjust the pH value to 9~10, then stir and filter it in room temperature to obtain 7-bromine-6-chlor-3-[3-[(2R,3S)-3-hydroxyl-2-piperidinyl]-2-oxypropyl]-4(3H)-quinazolinone (I) crude. The yield rate is 84.1%, with content by HPLC of 95.5% as well as C1: 0.5%, C2: 1.6% and C3: 1.1%.

Example 15

Take 20 g condensate (II), 3-[[(3aR,7aS)-N-CBZ-2-hydroxyl-Octahydro furan and [3,2-b]2-piperidinyl]methyl]-4(3H)-quinazolinone), dissolve it with 300 g 0.4N acetate-isopropyl alcohol solution (water content is 10%), add 1.5 g Ni—B non-crystalline alloy catalyst carried on aluminium oxide with a load of 10.0%, hydrogenate it under 60° C. and 1.0 Mpa hydrogen pressure, keep it in reaction for 30 hours, then filter it to recover Ni—B non-crystalline alloy catalyst, wash the catalyst with 50 ml isopropyl alcohol, reduce pressure to recover the solvent, add 300 ml water, adjust the pH value to 9~10, then stir and filter it in room temperature to obtain 3-[3-[(2R,3S)-3-hydroxyl-2-piperidinyl]-2-oxypropyl]-4(3H)-quinazolinone (I) crude. The yield rate is 87.2%, with contents by HPLC of 95.4% and C1: 2.1%.

Example 16

Take 20 g condensate (II), 3-[[(3aR,7aS)-N-CBZ-2-hydroxyl-Octahydro furan and [3,2-b]2-Piperidinyl]methyl]-4(3H)-quinazolinone), dissolve it with 250 g 0.4N formic acid-ethanol solution (water content is 10%), add 2 g Ni—B non-crystalline alloy catalyst carried on aluminium oxide with a load of 10.0%, hydrogenate it under 50° C. and 1.0 Mpa hydrogen pressure, keep it in reaction for 25 hours, then filter it to recover Ni—B non-crystalline alloy catalyst, wash the catalyst with 50 ml ethanol, reduce pressure to recover the solvent, add 300 ml water, adjust the pH value to 9~10, then stir and filter it in room temperature to obtain 3-[3-[(2R,3S)-3-hydroxyl-2-piperidinyl]-2-oxypropyl]-4(3H)-quinazolinone (I) crude. The yield rate is 89.1%, with content by HPLC of 95.8% and C1: 2.0%.

Example 17

Add 50 g 3-[3-[(2R,3S)-3-hydroxyl-2-piperidinyl]-2-oxypropyl]-4(3H)-quinazolinone (I) crude to the re-crystallization reactor, add 250 g mixed solvent consisting of 217 g methanol, 22 g water and 11 g bichloromethane, reflux for 8 hours, add appropriate amount of activated carbon for decoloring, stir for crystallization in 40° C. for 8 h, finally obtain the product 3-[3-[(2R,3S)-3-hydroxyl-2-piperidinyl]-2-oxypropyl]-4(3H)-quinazolinone (I). The yield rate is 72.7%, with contents by HPLC of 98.2% and C1: 0.2%.

Example 18

Add 50 g 3-[3-[(2R,3S)-3-hydroxyl-2-piperidinyl]-2-oxypropyl]-4(3H)-quinazolinone (I) crude to the re-crystallization reactor, add 500 g mixed solvent consisting of 333 g ethanol, 100 g water and 76 g trichloromethane, reflux for 8 hours, add appropriate amount of activated carbon for decoloring, stir for crystallization in 30° C. for 8 h, finally obtain the product 3-[3-[(2R,3S)-3-hydroxyl-2-piperidinyl]-2-oxypropyl]-4(3H)-quinazolinone (I). The yield rate is 78.1%, with content by HPLC of 98.6% and C1: 0.6%.

Example 19

Add 50 g 3-[3-[(2R,3S)-3-hydroxyl-2-piperidinyl]-2-oxypropyl]-4(3H)-quinazolinone (I) crude to the re-crystallization reactor, add 750 g mixed solvent consisting of 577 g isopropyl alcohol, 58 g water and 115 g carbon tetrachloride, reflux for 5 hours, add appropriate amount of activated carbon for decoloring, stir for crystallization in 15° C. for 8 h, finally obtain the product 3-[3-[(2R,3S)-3-hydroxyl-2-piperidinyl]-2-oxypropyl]-4(3H)-quinazolinone (I). The yield rate is 73.5%, with content by HPLC of 97.9% and C1: 0.2%.

Example 20

Add 50 g 7-bromine-6-chlor-3-[3-[(2R,3S)-3-hydroxyl-2-piperidinyl]-2-oxypropyl]-4(3H)-quinazolinone (I) crude to the re-crystallization reactor, add 750 g mixed solvent consisting of 555 g propyl alcohol, 167 g water and 28 g bichloroethane, reflux for 8 h, add appropriate amount of activated carbon for decoloring, stir for crystallization in 15° C. for 3 hours, finally obtain the product 7-bromine-6-chlor-3-[3-[(2R,3S)-3-hydroxyl-2-piperidinyl]-2-oxypropyl]-4(3H)-quinazolinone (I). The yield rate is 76.8%, with content by HPLC of 97.9% as well as C1: 0.3%, C2: 0.9% and C3: 0.4%.

Example 21

Add 50 g 7-bromine-6-chlor-3-[3-[(2R,3S)-3-hydroxyl-2-piperidinyl]-2-oxypropyl]-4(3H)-quinazolinone (I) crude to the re-crystallization reactor, add 300 g mixed solvent consisting of 230 g isopropyl alcohol, 46 g water and 24 g bichloroethane, reflux for 8 h, add appropriate amount of activated carbon for decoloring, stir for crystallization in 0° C. for 5 hours, finally obtain the product 7-bromine-6-chlor-3-[3-[(2R,3S)-3-hydroxyl-2-piperidinyl]-2-oxypropyl]-4(3H)-quinazolinone (I). The yield rate is 85.8%, with content by HPLC of 98.9% as well as C1: 0.2%, C2: 0.3% and C3: 0.1%.

Example 22

Add 50 g 7-bromine-6-chlor-3-[3-[(2R,3S)-3-hydroxyl-2-piperidinyl]-2-oxypropyl]-4(3H)-quinazolinone (I) crude to the re-crystallization reactor, add 500 g mixed solvent consisting of 370 g ethanol, 111 g water and 19 g bichloroethane, reflux for 8 hours, add appropriate amount of activated carbon for decoloring, stir for crystallization in 0° C. for 3 h, finally obtain the product 7-bromine-6-chlor-3-[3-[(2R,3S)-3-hydroxyl-2-piperidinyl]-2-oxypropyl]-4(3H)-quinazolinone (I). The yield rate is 87.9%, with content by HPLC of 99.0% as well as C1: 0.1%, C2: 0.2% and C3: 0.1%.

What is claimed is:
1. A method for preparing halofuginone compounds comprising the following steps:
(1) reacting a condensate of formula (II) for 12-35 hours in a catalytic hydrogenation solvent under 10~60° C. and 0.1~1.0 MPa controlled hydrogen pressure, with presence of a Ni—B non-crystalline alloy catalyst, as shown in the following reaction formula:

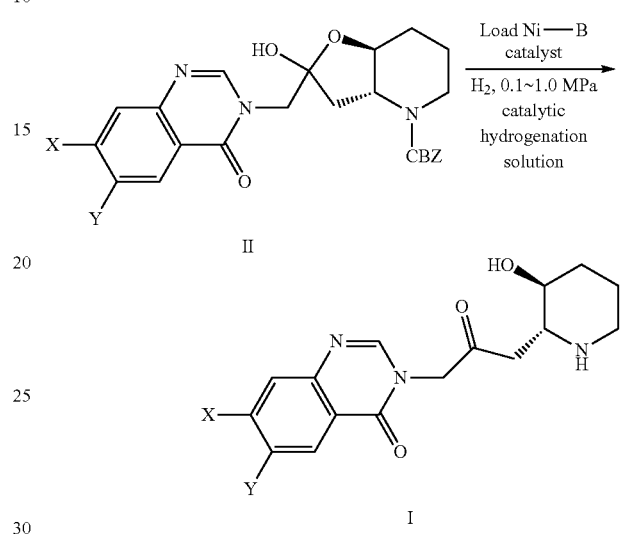

Halofuginone and its derivative
X = H, Y = H;
X = Br, Y = Cl;

wherein the Ni—B non-crystalline alloy catalyst is prepared by loading a Ni—B non-crystalline alloy on an aluminium oxide or zeolite carrier, with a load of 1.0~20.0% as a weight percentage;
wherein the weight ratio between the Ni—B non-crystalline alloy catalyst and the condensate (II) is 1:10~40;
wherein the catalytic hydrogenation solvent is a 0.1~0.6N acidic aqueous alcohol solution containing a mass of the catalytic hydrogenation solvent being 8-20 times that of the condensate (II);
wherein the Ni—B non-crystalline alloy catalyst is prepared as follows: adding a nickel salt into an aqueous solvent until the salt is dissolved; then adding a carrier selected from the group consisting of aluminium oxide and zeolite; adding a KBH4 solution drip by drip under 0~30° C.; after above reaction is over, filtering the solution, washing precipitates with deionized water until pH reaches 6.5~7.5, and finally storing treated precipitates in anhydrous ethanol for use; the nickel salt above is $Ni(NO_3)_2$, $NiCl_2$ or $Ni(SO_4)$;
(2) filtering the Ni—B non-crystalline alloy catalyst and treating yielded filtrate to obtain crude 3-[3-[(2R,3S)-3-hydroxyl-2-piperidinyl]-2-oxypropyl]-4(3H)-quinazolinone compounds (I);
(3) through refining procedures, obtaining refined 3-[3-[(2R,3S)-3-hydroxyl-2-piperidinyl]-2-oxypropyl]-4(3H)-quinazolinone compounds (I);
wherein the refining procedures are as follows: adding the crude 3-[3-[(2R,3S)-3-hydroxyl-2-piperidinyl]-2-oxypropyl]-4(3H)-quinazolinone compounds to a re-crystallizing solvent for reflux for more than 8 hours, then decolorizing it with activated carbon and crystallizing it under 0~40° C. for 3-8 hours to obtain refined product;

wherein the re-crystallizing solvent is a mixed solution of alcohol, water and halohydrocarbon, the amount of the mixed solution is 5-15 times of the amount of the crude 3-[3-[(2R,3S)-3-hydroxyl-2-piperidinyl]-2-oxypropyl]-4(3H)-quinazolinone derivative compounds in weight;

wherein the ratio of the mixed solvent for the re-crystallization is: the mass ratio of alcohol:water:halohydrocarbon=1:0.1~0.3:0.05~0.2;

wherein the alcohol used in the solvent for the re-crystallization is C1~C4 alcohol;

wherein the halohydrocarbon used in the solvent for the re-crystallization is dichromethane, trichloromethane, dichroethane or carbon tetrachloride.

2. The method according to claim 1, wherein said catalyst is the Ni—B non-crystalline alloy catalyst prepared by loading the Ni—B non-crystalline alloy on the aluminium oxide or zeolite carrier, with a load of 1.0~10.0% as weight percentage.

3. The method according to claim 1, wherein the mass ratio between the Ni—B non-crystalline alloy catalyst and the condensate (II) is 1:10~20.

4. The method according to claim 1, wherein the number of re-using said Ni—B non-crystalline alloy on the aluminium oxide or zeolite carrier for 5-10 times.

5. The method according to claim 1, wherein the mass required for the catalytic hydrogenation solvent is 8-15 times that of the condensate (II).

6. The method according to claim 1, wherein acid used in the said catalytic hydrogenation solvent is $H_2SO_4$, hydrochloric acid, formic acid or acetate.

7. The method according to claim 1, wherein said catalytic hydrogenation solvent is 0.1~0.4N acidic aqueous alcohol solvent, and the alcohol is methanol, ethanol, isopropyl alcohol, n-butanol, isobutanol, tert-butanol or amyl alcohol;

wherein the mass of water contained in said aqueous alcohol solvent is 5~30% that of the alcohol.

8. The method according to claim 1, wherein the hydrogen pressure during catalytic hydrogenation is 0.1~0.6 Mpa and the catalytic hydrogenation temperature is 10~60° C.

9. The method according to claim 1, wherein said catalytic hydrogenation time is 15-25 hours.

10. The method according to claim 1, wherein the ratio among nickel salt, carrier and KBH4 during step (1), the preparation process of the Ni—B non-crystalline alloy catalyst, is 0.02~1.0:0.8~1.2:1.0 (in mol), and the temperature for reduction reaction is 0~10° C.

11. The method according to claim 1, wherein the selected re-crystallizing solvent as described in step (3) is the mixed solution of alcohol, water and halohydrocarbon, and the amount of the mixed solution is 5-10 times of the amount of the crude 3-[3-[(2R,3S)-3-hydroxyl-2-piperidinyl]-2-oxypropyl]-4(3H)-quinazolinone compounds in weight.

12. The method according to claim 1, wherein the alcohol used in the re-crystallizing solvent as described in step (3) is methanol, ethanol, isopropyl alcohol or propyl alcohol.

13. The method according to claim 1, wherein the crystallization temperature as described in step (3) is 0~15° C. and the crystallization time is 3-5 hours.

\* \* \* \* \*